(12) United States Patent
Mahalingam et al.

(10) Patent No.: US 8,508,238 B2
(45) Date of Patent: Aug. 13, 2013

(54) SYSTEM AND METHOD FOR PERFORMING ELECTRICAL IMPEDANCE TOMOGRAPHY

(75) Inventors: Sakethraman Mahalingam, Bangalore (IN); Manoj Kumar Koyithitta Meethal, Bangalore (IN); Prafull Sharma, Bangalore (IN); Rajesh Veera Venkata Lakshmi Langoju, Bangalore (IN); Wrichik Basu, Bangalore (IN); Parama Ghoshal, West Bengal (IN)

(73) Assignee: General Electric Company, Niskayuna, NY (US)

( * ) Notice: Subject to any disclaimer, the term of this patent is extended or adjusted under 35 U.S.C. 154(b) by 230 days.

(21) Appl. No.: 12/855,018

(22) Filed: Aug. 12, 2010

(65) Prior Publication Data

US 2012/0038368 A1 Feb. 16, 2012

(51) Int. Cl.
*G01R 27/02* (2006.01)

(52) U.S. Cl.
USPC .......................... 324/603; 324/609; 324/71.1

(58) Field of Classification Search
USPC .............. 324/451–453, 71.1, 698; 73/304 R, 73/304, 305–308
See application file for complete search history.

(56) References Cited

U.S. PATENT DOCUMENTS

| | | | |
|---|---|---|---|
| 4,063,153 A | 12/1977 | Dechene et al. | |
| 4,539,640 A | 9/1985 | Fry et al. | |
| 4,920,490 A | 4/1990 | Isaacson | |
| 4,975,645 A | 12/1990 | Lucas | |
| 5,284,142 A | 2/1994 | Goble et al. | |
| 5,291,791 A | 3/1994 | Lucas et al. | |
| 5,351,697 A | 10/1994 | Cheney et al. | |
| 5,381,333 A | 1/1995 | Isaacson et al. | |
| 5,396,806 A | 3/1995 | Dechene et al. | |
| 6,218,846 B1 | 4/2001 | Ludwig et al. | |
| 6,236,886 B1 | 5/2001 | Cherepenin et al. | |
| 6,272,915 B1* | 8/2001 | Kostelnicek et al. | 73/152.28 |
| 6,548,771 B1* | 4/2003 | Tokoro | 200/61.47 |
| 7,167,009 B2 | 1/2007 | van Schoor et al. | |
| 2003/0016001 A1 | 1/2003 | Borup | |
| 2003/0085715 A1 | 5/2003 | Lubkeman et al. | |
| 2005/0024099 A1 | 2/2005 | Ross et al. | |
| 2006/0265150 A1 | 11/2006 | Hu et al. | |
| 2007/0133746 A1 | 6/2007 | Ortiz Aleman et al. | |
| 2011/0162448 A1* | 7/2011 | McGaughey et al. | 73/304 C |

FOREIGN PATENT DOCUMENTS

| | | |
|---|---|---|
| WO | 02053029 A1 | 7/2002 |
| WO | WO2008118727 A1 | 10/2008 |

OTHER PUBLICATIONS

Pinheiro et al., "Three-Dimensional Electrical Resistance Tomography in a Stirred Mixing Vessel", Chemical Engineering Communications, vol. 175, pp. 25-38, Jan. 1, 1999.

Fabrizi et al., "An electrode addressing protocol for imaging brain function with electrical impedance tomography using a 16-channel semi-parallel system" Physiological Measurement, vol. 30, No. 6, pp. S85-S101, Jun. 1, 2009.

(Continued)

*Primary Examiner* — Vincent Q Nguyen
(74) *Attorney, Agent, or Firm* — Jason K. Klindtworth (57) ABSTRACT

An electrode array, a system and a method for reconstructing the distribution of electrical properties within a multi-material object. One embodiment includes electrodes arranged along a three-dimensional helical path to provide one or more helical arrays and circuitry to measure signals for calculating a conductivity or admittivity distribution representative of the interior of the structure. Image data may be obtained which is representative of the multi-material region.

20 Claims, 4 Drawing Sheets

(56) References Cited

OTHER PUBLICATIONS

Fabrizi et al., "A comparison of two EIT systems suitable for imaging impedance changes in epilepsy" Physiological Measurement, vol. 30, No. 6, pp. S103-S120, Jun. 1, 2009.
Jaworek et al., "Gas/liquid ratio measurements by rf resonance capacitance sensor" Sensors and Actuators, vol. 113, No. 2, pp. 1-7, Jul. 5, 2004.
W.Q.Yang et al., "Development of Capacitance Tomographic Imaging Systems for Oil Pipeline Measurements", Review of Scientific Instruments, vol. 66, No. 8, pp. 4326-4332, Aug. 1995.
J.A. Kjell et al., "Comparison of Different Measurement Protocols in Electrical Capacitance Tomography using Simulations", IEEE Transactions on Instrumentation and Measurements, vol. 56, No. 6, pp. 2119-2130, Dec. 2007.
M.S. Rocha et al., "Void Fraction Measurement and Signal Analysis from Multiple-Electrode Impedance Sensors", Heat Transfer Engineering, vol. 29, No. 11, pp. 924-935, Jan. 2008.
C-N. Huang et al., "Rotational Electrical Impedance Tomography", Measurement Science and Technology, vol. 18, pp. 2958-2966, Aug. 2007.
Search Report and Written Opinion from corresponding EP Application No. EP10196465.8 mailed on Aug. 28, 2012.
D. C. Dobson et al., "Resolution and Stability Analysis of an Inverse Problem in Electrical Impedance Tomography: Dependence on the Input Current Patterns," vol. 54, pp. 1-19, 1994.
J. H. Kim et al., "Directional Algebraic Reconstruction Technique for Electrical Impedance Tomography," Journal of the Korean Physical Society, vol. 54, No. 4, pp. 1439-1447, Apr. 2009.
Mohd. Zaid Abdullah, "Simulation of an Inverse Problem in Electrical Impedance Tomography Using Resistance Electrical Network Analogues", International Journal Electrical Engineering Education, vol. 36, pp. 311-324, 1999.
J. H. Calderwood et al., "A novel field for possible use in medical impedance tomography"; Journal of Medical Engineering & Technology, vol. 22, No. 3, pp. 121-125, May/Jun. 1998.
J. Gu et al., "A New Resistor Network Based Forward Model for Electrical Impedance Tomography Sensors"; I2MTC 2009—International Instrumentation and Measurement, 4 pages, May 5-7, 2009.
L M Heikkinen et al., "Real time three-dimensional electrical impedance tomography applied in multiphase flow imaging," Institute of Physics Publishing, Measurement Science Technology, vol. 17, pp. 2083-2087, Jul. 2006.
Search Report and Written Opinion from corresponding EP Application No. 11175909.8-2204 dated Nov. 21, 2011.
P.A.T. Pinheiro et al., "Three-Dimensional Electrical Resistance Tomography in a Stirred Mixing Vessel", Chemical Engineering Communications, vol. 175, pp. 25-38, 1999.
A. Jaworek et al., "Gas/liquid ratio measurements by rf resonance capacitance sensor", Sensors and Actuators A Physical, vol. 113, No. 2, pp. 133-139, 2004.
L. Fabrizi et al., "An electrode addressing protocol for imaging brain function with electrical impedance tomography using a 16-channel semi-parallel system," Physiological Measurement, vol. 30, pp. S85-S101, 2009.
L. Fabrizi et al., "A comparison of two EIT systems suitable for imaging impedance changes in epilepsy", Physiological Measurement, vol. 30, pp. S103-S120, 2009.
Search Report and Written Opinion from corresponding EP Application No. 101966388.0-2204 dated Apr. 28, 2011.
M. Cheney et al., "Distinguishability in Impedance Imaging," IEEE Transactions on Biomedical Engineering, vol. 39, No. 8, Aug. 1992, pp. 852-860.
S.F. Gull, et al; "Maximum Entropy Tomography"; Applied Optics vol. 25, No. 1; Jan. 1986.
Cheney, et al., "NOSER: An Algorithm for Solving the Inverse Conductivity Problem"; International Journal of Imaging Systems and Technology. vol. 2 66-75 (1990).
Kapinos; "Multivariate Differentiation of Constrained Optimization: A Primer"; Wesleyan.edu; Economics 110; Fall 2004.
Calderwood, et al; "The provision of an electrical field of controllable penetration into a cylinder"; Institute of Physical Sciences in Medicine; vol. 13; Supl. A 145-149 1992.
B. Raphael, et al; Appl Math Comput; 146 (203) 729-758, 2003.
Raphael; et al; A Direct Stochastic Algorithm for Global Search; IMAC EPFL—Federal Institute of Technology, Lausanne CH 1015, pp. 729-745;2002.

\* cited by examiner

SYSTEM AND METHOD FOR PERFORMING ELECTRICAL IMPEDANCE TOMOGRAPHY

BACKGROUND

This invention relates generally to non-destructive or non-invasive evaluation of a multi-material object and, more specifically, to methods for generating data for performing Electrical Impedance Tomography of an object comprising different materials within a closed boundary, referred to as a multi-material object.

The principles of Electrical Impedance Tomography (EIT) are based on knowledge that objects under examination have variations in electrical properties, e.g., conductivities and permittivities, which are highly correlated with material characteristics such as density or chemical composition. For example, in the human body there are significant variations in electrical conductivity among body tissues.

In industrial activities and other non-clinical applications, it is desirable to perform non-invasive monitoring or imaging to determine the composition of a body volume, or to characterize the size and shape of a feature, or other condition within an object of interest. Generally, EIT is useful for imaging features within a volume that are characterized by distinguishable electrical properties. However, EIT can also be used in a manner where, instead of generating an image, the end-result may be a mathematical value or a set of mathematical values indicative of the location, proportions or other properties of the different materials within the volume. For example, features within volumes having different densities can be resolved on this basis. For example, in multiphase fluid mixtures it is known that conductivities will vary based on phase (e.g., liquid or gas) or chemical composition. In principle, electrical measurements performed with relatively simple instrumentation can provide data indicative of (i) where in the volume a particular material is located, (ii) the relative proportions of different constituents and (iii) the shape of the boundary between different materials within the volume. Examples of mixtures for which phase concentrations can be determined are solid-liquid compositions such as slurries, gas-liquid compositions such as present in oil pipelines, and, generally, liquid-liquid and solid-gas-liquid mixtures. The mixtures may be stationary or flowing. In the case of fluids flowing through a pipe, conductivity determinations among materials of different phases, or between materials having different chemical properties (e.g., water and oil), can lead to determinations of relative volumes present.

Generally, there is a need to determine internal flow characteristics in these types of multiphase flow processes as this information enables improved design and control of industrial processes and increased operational efficiency of existing and new processing equipment. Flow characteristics used to predict performance of multiphase processes may include, for example, spatial distributions of the phases (spatial volumetric phase fractions), flow regimes, definition of interfacial areas, and determination of absolute and relative velocities between the phases or materials. Knowing the spatial distribution of the materials is particularly useful since non-uniform distributions of the materials tend to reduce the interfacial area between materials available for chemical reaction or conversion and may result in recirculating flows creating spatially non-uniform reaction zones or concentrations. Further, the volumetric phase fraction and velocity are important parameters that enable proper and timely control of multiphase flows.

With respect to determining volume fractions of liquid and gas phases in a pipe using EIT, it is conventional to acquire data by placing a series of electrodes along the periphery of a body under study, e.g., in a circle along an interior surface of a pipe. See U.S. Pat. Nos. 4,486,835; 4,539,640; 4,920,490; and 5,381,333, all of which are incorporated herein by reference. In the systems described by the foregoing literature, a set of electrical signals (voltage or current) are applied to the volume via electrodes. The measured electrical signals (voltage or current) are used to reconstruct spatial features within the volume under study so that an image representative of the features can be generated. In this regard, there is what is often referred to as an inverse problem wherein there may not be a unique solution, i.e., image, corresponding to the acquired data. The set of applied electrical signals is typically a series of excitation patterns. It is necessary to sequentially drive the set of electrodes with a relatively large series of such excitation patterns. As an example, in one of the excitation patterns in the series all the electrodes may be applied with sinusoidal voltage signals that are phase shifted with respect to one another. Corresponding current signals are measured in response to each set of excitation patterns. Using data acquired from application of the series of excitation patterns, algorithms are applied to find a distribution of electrical properties within the volume and hence the distribution of various materials.

When the electrodes are positioned along a selected plane cutting through the body under study, the algorithms are intended to provide a distribution of the electrical properties along the same plane. Generally, a wide variety of mathematical methods and numerical techniques have been applied to determine the distribution of electrical properties representative of the multi-material object along the selected plane. Noting that currents spread into the third dimension (out of the plane along which the electrodes are placed) as they travel through a structure under examination, details of fine structures may not be easily resolved.

BRIEF DESCRIPTION OF THE INVENTION

In one embodiment of the invention an electrode array is provided for use in generating and measuring electrical signals. The array is suited for reconstructing the distribution of electrical properties within a multi-material object in an interior region of a structure. Such a region may be characterized by materials having different conductivities or admittivities which influence transmission of electrical signals through the region. The electrode array includes a plurality of electrodes arranged along at least one three-dimensional helical path to provide one or more helical arrays of electrodes about the multi-material region.

According to another embodiment of the invention, a method is provided for generating data for reconstructing the distribution of electrical properties within a multi-material object. A plurality of electrodes is configured along a three-dimensional helical path to provide a three dimensional array of electrodes about the multi-material object. A set of signal patterns is applied to the electrodes. In response to application of the set of signal patterns, a measured set of electrical signals is obtained from the electrodes. In example embodiments, numerous types of electric field patterns are sequentially generated within the multi-material object.

There is also provided an electrical impedance tomography system for generating and measuring electrical signals for reconstructing the image of a multi-material region in the interior of a structure. The region may be characterized by materials having different conductivities or admittivities which influence transmission of electrical signals through the region. The system includes a plurality of electrodes arranged along at least one three-dimensional helical path to provide one or more helical arrays of electrodes that may be positioned about the multi-material region. The system also includes processing circuitry to obtain, in response to application of a set of signal patterns, a measured set of electrical signals from the electrodes suitable for calculating a conductivity or admittivity distribution representative of the interior of the structure in a region of the structure about which the electrodes are positioned. According to embodiments the system may determine image data representative of the multi-material region in the structure including two or more regions having different conductivities or admittivities. Also according to example embodiments, measured data may be used to reconstruct an image of a multi-material object for display on a monitor or further electronic transmission.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The invention is now described in an application where the distribution of electrical properties within a multi-material object can be used to determine proportions of components in a multiphase flow. In this example multiple materials are flowing together inside a pipe or a conduit. Embodiments of the present invention function to provide a system and a method for measuring the characteristics of multi-material systems, such as those used in the oil industry, to estimate fractions and flow rates of oil, water, and hydrocarbon gases flowing through pipes. Although the invention is described with reference to a use in oil/gas/water measurements, it is by no means limited to such applications. Rather, the invention is applicable to a wide variety of industrial, healthcare and chemical processes such as, for example, medical imaging, cancer diagnosis and water treatment processes.

Multiple material flow through the pipe may include two or more physical states of solid, liquid and gas. Accurate characterization of multiphase flow processes enables improved design and increased operational efficiencies of systems and processing equipment used in the petroleum, pharmaceutical, food, and chemical industries. Relevant flow characteristics used to predict performance of multiphase processes may include, for example, spatial distribution of the phases (spatial volumetric phase fractions), flow regime characterization, interfacial area, and absolute and relative velocities between different phases or materials. With an ability to more accurately determine non-uniform spatial distribution of materials in a multi-phase flow, it becomes possible to manage and control the process for a more desirable outcome. For example, in a pipeline carrying petroleum products the proportion of gas relative to liquid constituent may be minimized. In coal slurry transport, the volumetric proportion of water to coal can be optimized to assure maximum achievable energy content per unit volume. As another example, applicable to optimizing manufacturing processes, it is important to monitor and reduce non-uniform distributions of materials undergoing chemical reaction or conversion. Such processes may have reduced interfacial area between materials due to, for example, recirculating flows that create spatially non-uniform reaction zones or concentrations.

Thus real-time knowledge of volumetric phase fractions and associated components enable timely and effective control of multi-phase processes. However, computational requirements to generate such characterizations can add undue complexity and may delay the response time needed to implement timely control of the process being monitored. For this reason many of the prior systems have relied upon approximations to determine the material proportions and to characterize the separation of materials in a multi-phase system.

A typical EIT system may be based on sequential application of input signals to pairs of electrodes and sensing of signals in response thereto at one or more other electrodes. For example, currents may flow between a pairs of electrodes, one pair at a time, with voltages being measured on the remaining electrodes. Alternately, voltages may be applied across the pairs of electrodes, one pair at a time, with current measured at one or more of the other electrodes. According to example embodiments of the invention, relatively large amounts of electrical data are more quickly acquired by simultaneously applying currents or voltages to all of the electrodes. The applied currents or voltages may have predefined phase or frequency shifts or may be electrically in phase with each other and may have amplitude variations. With generation of the increased amount of electrical data, it is possible to realize a higher signal-to-noise ratio and a higher resolution. Specific electric field patterns are developed within the multi-material object when the electrodes are excited with specific signal patterns. This electric field patterns can be flexibly controlled, focused and modified when all the electrodes are simultaneously excited. This is especially relevant when the body under examination comprises components with small variations in relative permittivities or conductivities, as a relatively larger number of measurements are needed to provide necessary resolution.

When generating electrical data with current signals to reconstruct images with EIT, the currents, injected into the volume being imaged generally do not travel in straight lines from electrode to electrode. Rather, the currents spread, taking multiple paths that often involve all three dimensions. Assumptions that currents through a volume travel along straight or curved lines within two dimensions, such as the plane in which a set of electrodes are positioned, can result in errors due to improper characterizations of current flow paths. Poorer quality images, i.e., wherein details of fine structures cannot be easily resolved, result from currents spreading into the third dimension (out of the plane along which the electrodes are placed) as the currents travel through a structure under examination. For example, electrical current may follow a path out of the plane in which the electrodes are positioned, around regions of material in the plane having lower electrical conductivities. In such situations, the resolution of the EIT technique is severely degraded because the measured electrical signals are not only indicative of the material distribution in the plane of the electrodes but also of the material distribution outside the plane in which the electrodes are placed. Therefore, it is desirable to find techniques by which improved interrogation of the multi-material object can be made so that the three dimensional multi-material object under evaluation can be thoroughly interrogated and the internal material distribution clearly determined with higher resolution.

Figure 1:
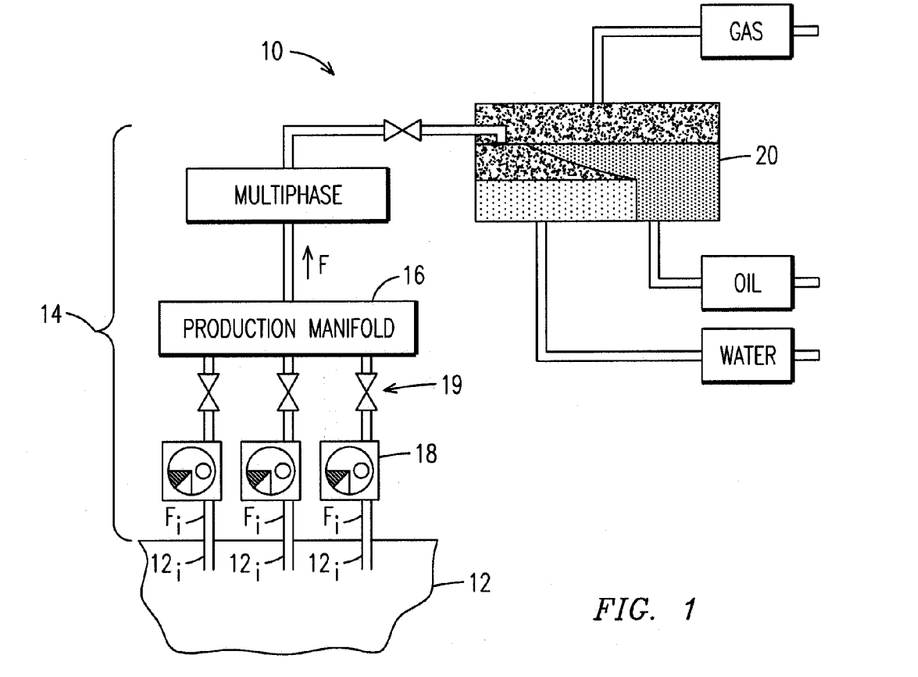
FIG. 1 is a block diagram of a oil production facility according to an example embodiment.

With reference to the simplified schematic diagram illustrated in FIG. 1, an example embodiment of the invention is described for a typical oil production facility 10 having multiple oil wells $12_i$ connected to a piping system 14. The piping system 14 includes a production manifold 16 coupled to receive flow $F_i$ from each well $12_i$ and output a total flow F. The flow $F_i$ from each well passes through a multi-phase flow meter (MPFM) 18 according to the invention before entering the manifold 16 and may be controlled by a valve system 19 to regulate the overall proportion of, for example, liquid and gaseous phases.

Each multi-phase flow meter is part of a system that enables measurement of unprocessed well streams close to the well and can thus provide continuous monitoring of well performance. Information processed by each multi-phase flow meter system may be used for better reservoir management and flow control. Fluids pumped from the oil wells $12_i$ are sent to a production separator 20 through the production manifold 16. A test separator (not shown) may be incorporated with the multiphase flow meter systems. One advantage of a multiphase flow meter system over a test separator is the reduced time needed to characterize the composition of the flow.

The production separator 20 separates oil, gas and water pumped from the wells. The production separator 20 may further include one or multiple measurement devices including, for example, a water meter to measure an amount of water or a rate at which water extracted from a well, and an emulsion meter to measure an amount of oil extracted from the well. Other typical measurement devices include a wellhead pressure sensor and a thermometer.

Figure 2:
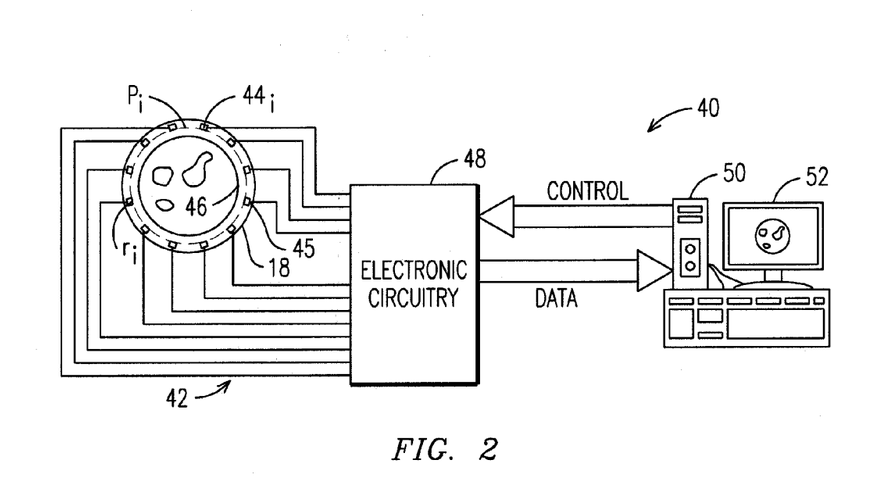
FIG. 2 is a schematic of an electrical impedance tomography (EIT) based imaging system incorporating a multiphase flow meter in accordance with an embodiment of the present invention.

Next, referring to the simplified schematic diagram of FIG. 2, a partial view is shown of an electrical impedance tomography (EIT) image reconstruction system 40 incorporating one of the MPFM's 18 of FIG. 1. According to an example embodiment of the invention, the system 40 is configured to generate images based on conductivity reconstruction. However, it is to be understood that, in principle, EIT image reconstruction may be based on conductivity and/or permittivity (sometimes referred as admittivity). With the system 40, conductivities and/or permittivities of materials being observed are inferred based on boundary electrical measurements taken from electrodes near the periphery of the volume under study as each set of current or voltage signals is applied to the electrodes.

According to one group of example embodiments, large amounts of data are acquired by obtaining measurements from all electrodes for each in a series of multiple sets of signals. That is, measurements are repeated for numerous different configurations or patterns of applied currents and/or voltages. When one or more sets of time varying signals are applied, data are periodically acquired from the electrodes.

The illustrated MPFM system 40 includes wiring 42 connecting L electrodes $44_i$ to electronic circuitry. The electrodes $44_i$ are distributed along a surface 45 of a conduit 46 as more fully illustrated in FIGS. 3 and 4. In the example embodiment, the surface 45 is of a generally cylindrical shape formed about a central axis of symmetry 47. Although not expressly shown, the conduit 46 is positioned in line between one of the oil wells $12_i$ and the manifold 16 of FIG. 1 so that multiphase components pass through the conduit. The electrodes $44_i$ are formed as a set of p helical arrays, $H_j$, with j ranging from 1 to p. More generally, the electrodes may be formed as an ordered array along one or multiple helical paths. In the illustrated embodiment having L electrodes formed in p arrays, each array comprises a sequence of r electrodes $44_i$, with i ranging from 1 to r, formed along a helical path. As is well known, helical shapes formed about three dimensional surfaces, e.g., cylindrical or spherical surfaces, may be of a regular form which can be analytically described, or may be irregular spiral geometries. The embodiments described herein comprise electrodes positioned along helical paths having regular shapes for which the paths about the surface 45 can be described with simple mathematics. It is to be understood that in other embodiments the electrodes $44_i$ may be distributed along more complex paths, including paths of irregular shapes.

Figure 3:
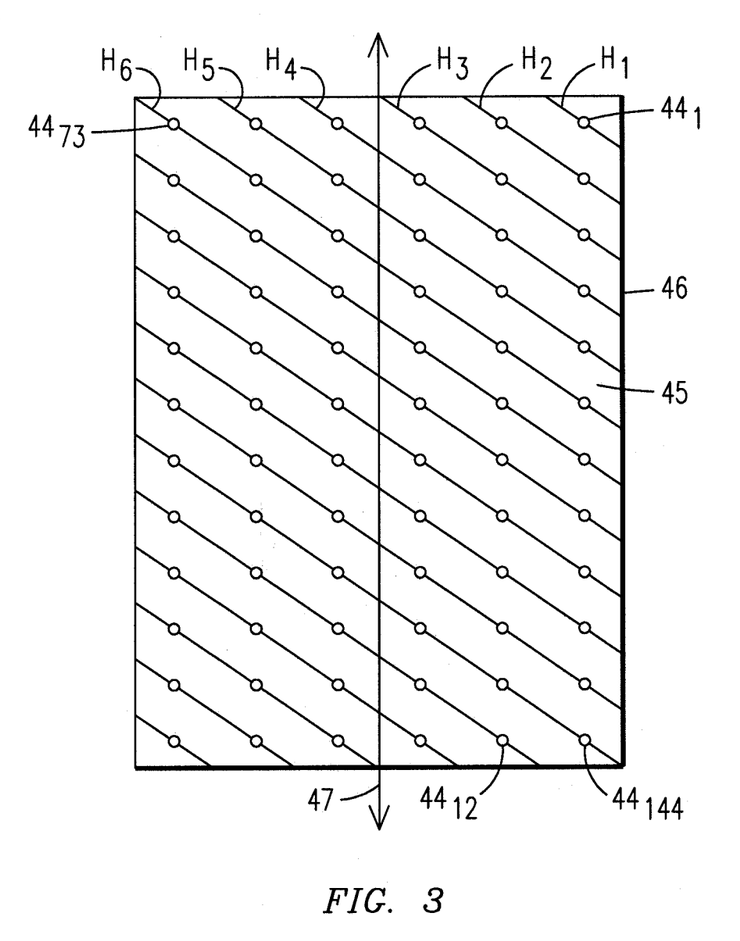
FIG. 3 is a side view of a series of electrodes positioned in helical arrays on a flow meter in accordance with an embodiment of the present invention.
Figure 4:
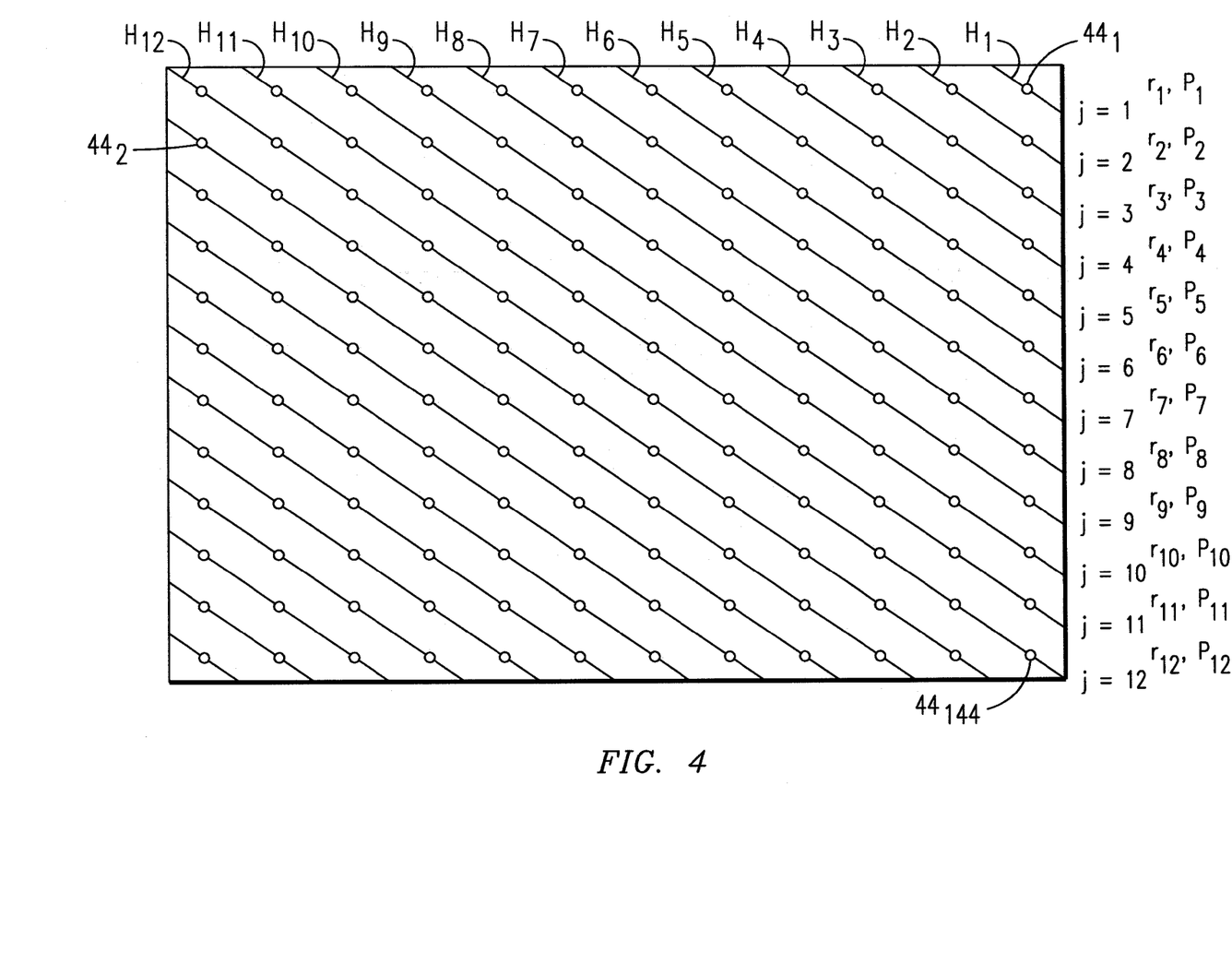
FIG. 4 is an unrolled view of the helical arrays shown in FIG. 3.

FIG. 3 provides a side view of the MPFM 18 showing p=12 helical arrays symmetrically winding about the conduit 46. FIG. 4 presents a 360 degree view of the 12 helical arrays shown in FIG. 3. The view of the helical arrays shown in FIG. 4 is a transform from the three dimensional contours about the cylindrically shaped conduit 4 to views in a plane, referred to herein as an "unrolled" view. That is, the view of FIG. 4 is generated as though the three dimensional shaped surface is cut open and laid along a plane to provide a two dimensional or plan view in which the abscissa represents the circumference around the conduit 46 and the ordinate is along the axial direction.

In the disclosed embodiments each array $H_j$ is formed along the path of a regular helix. FIGS. 3 and 4 illustrate with solid lines each of the helical paths along which, for j=1-12, each of the helical arrays $H_j$ is formed. The electrodes $44_i$ are illustrated as dots along each helical path. For j=1, a first electrode, $44_1$, is positioned in the ring r=1 along the plane $P_1$, on the array $H_1$ and a last electrode $44_{144}$ is positioned in the ring r=12 along the plane $P_{12}$, on the array $H_{12}$. The helical paths, along which electrodes in the arrays are positioned, may be generated in accord with the relationships of Equations 1A, 1B and 1C for a regular, non-tilted helix in three-dimensional space:

$$X(\theta)=[h/(2*\pi)]\theta \qquad \qquad 1A$$

$$Y(\theta)=R\cos(\theta) \qquad \qquad 1B$$

$$Z(\theta)=R\sin(\theta) \qquad \qquad 1C$$

where the X coordinate is along a longitudinal direction parallel with the axis 47 and the Y and Z coordinates are along directions transverse to the axis 47 and orthogonal to one another. θ is the azimuthal angle measured in a Y-Z plane transverse to the X-axis. The parameter h defines the advance per turn in the X direction. R is the radius of the helical path relative to an axis of symmetry of the conduit 46. That is, for embodiments having a regular shape, R corresponds to a radial distance from the axis 47 to a point on the path along the surface 45.

Three-dimensional space curves for the helical paths may also be regular helical geometries generated in accord with the relationships of Equations 2A, 2B and 2C:

$$X(\theta)=[h/(2*\pi)]\theta+A_n\sin(n\theta) \qquad \qquad 2A$$

$$Y(\theta)=R\cos(\theta) \qquad \qquad 2B$$

$$Z(\theta)=R\sin(\theta). \qquad \qquad 2C$$

The term $A_n\sin(n\theta)$, in the $X(\theta)$ equation, is a modulating component which imparts a positive or a negative tilt to each of the turns relative to the Y-Z plane, in proportion to the magnitude and sign of the term $A_n$. According to the value of n, the term $A_n \sin(n\theta)$ also introduces a modulation, i.e., a sinusoidal variation, in each 360 degree turn of the curve (i.e., helical path) about the axis. For n=1, an ellipsoidal shape is imparted to each turn. More complex patterns, having sinusoidal components corresponding to n>1 may be suitable for design of the helical paths along which the electrodes are placed. With addition of the $A_n \sin(n\theta)$ term and with n=1, the helical paths include a tilt relative to planes orthogonal with the X axis, e.g., the axis of symmetry of the conduit 46.

Still, more generally, a three-dimensional space curve of a helical-shaped path may be generated in accord with the equations 3:

$$X(\theta)=[h/(2*\pi)]\theta \pm \Sigma A_n f_1(n\theta) \quad \quad 3A$$

$$Y(\theta)=Rf_2(\theta) \quad \quad 3B$$

$$Z(\theta)=Rf_3(\theta) \quad \quad 3C$$

wherein $f_1$, $f_2$ and $f_3$ are arbitrary functions which may be trigonometric or numerical expressions but are not so limited. Also, the helical paths along which the electrodes are positioned are illustrated in the drawings as each making a single turn about the axis 47, but it is to be understood that the number of revolutions which the path takes about the axis is a design choice.

The example embodiments of the electrode arrays are highly symmetric, but numerous non-symmetric distributions of electrodes $44_i$ within and between the different arrays $H_j$ may be had. For the illustrated embodiment, the electrodes $44_i$ in each sequence of r electrodes in each helical array $H_j$ are spaced equidistant from a next or previous electrode $44_i$ in the same array $H_j$. This equidistant spacing between electrodes in each array is the same as the equidistant spacing between electrodes in each other array. Moreover, the arrays $H_j$ are spaced apart along the surface 45 by a predetermined phase angle. Thus, in the given example, with p=12, each array is rotationally spaced 30 degrees apart, about the axis 47, from a next or previous array. With the equidistant spacing between electrodes in different helical arrays, this results in circular sets of electrodes, i.e., a series of circular-like rings, R, each comprising p=12 electrodes, with each ring R spaced equidistant from a next or previous ring R and with the 12 electrodes in each ring positioned 30 degrees apart, about the axis 47, along the conduit surface 45 in a circular pattern. For example, with the conduit having a height, h, measurable along the axis 47, the spacing between each ring R can be set at h/12. FIG. 4 illustrates each of 12 rings $r_i$ (i=1-12) each formed along a different plane $P_i$.

In FIG. 2, the view of the MPFM 18 is in cross section along a plane $P_i$ cutting through one such ring $r_i$. The exemplary ring $r_i$ comprises one electrode $44_i$ from each of the twelve exemplary helical arrays $H_j$. For purposes of illustrating the invention, the helical arrays collectively comprise 144 electrodes $44_i$ formed about the cylindrical surface 45 of the conduit 46 in the arrangement of 12 rings. However, the total number, L, of electrodes positioned about a volume to be imaged may be fewer than or more than 144, depending in part on the size of the volume under study and the desired image resolution. In one embodiment, each of the electrodes $44_i$ may be mounted along the inner wall of the conduit 46 with an electrical connection via the wiring 45 from an external signal source passing through the outer wall to connect with the electrode. A coating may be applied to each electrode to reduce contact resistance between the electrode and media flowing through the conduit 46.

The 12 electrodes $44_i$ are shown in FIG. 2 as configured in a circular arrangement along the cylindrical surface 45 of the conduit 46 and in a plane, $P_i$, which cuts through the central axis 47. In this example, and the figures generally, the plane $P_i$ is orthogonal to the axis 47, but the rings R may be cut through the axis 47 at variable angles. Also, the helical arrays $H_i$ may be formed along other three dimensional surfaces such as surfaces having spherical or elliptical contours. The rings R do not have to be circular in shape.

FIG. 2 illustrates connections of the 12 electrodes $44_i$ in the ring R with the signal source and this is exemplary of connections of all electrodes $44_i$ with the signal source through the wiring 45 to electronic circuitry 48 which includes, e.g., for each electrode: a current or voltage source, a D-to-A-converter, an A-to-D converter, a differential amplifier and one or more filters. The circuitry 48 further includes analog multiplexers, clock circuitry, and/or a digital I/O unit coupled to a computer 50 in order to provide sets of input signals to the electrodes. Specific arrangements for the circuitry 48 are known in the art and not further described herein because illustration of the invention does not require illustration of specific circuit designs.

The computer 50 may comprise high speed processors, including a conventional digital signal processor of the type used for the image reconstruction, and a suitable display 52 for viewing images generated according to the invention. Other processing circuitry such as field-programmable gate arrays (FPGA's) and complex programmable logic devices (CPLD's) may be incorporated in the computer 50 or in other portions of the system 40.

When each set of electrical signals is applied to the electrodes $44_i$ of one of the helical arrays $H_j$, the electric field produced within the volume enclosed by the surface 45 turns in a helical, i.e., screw-like, fashion. The signals applied to different ones of the helical arrays $H_j$ can be varied in a coordinated manner, e.g., with defined phase relationships, to augment the time-varying pattern generated by one of the helical arrays $H_j$. The following exemplary discussion assumes that voltage signals are applied to the electrodes and that current signals are acquired in response thereto in order to generate needed data for image reconstruction. The voltage sources are used to apply each set of patterns to the electrodes $44_i$, and the corresponding set of current signals in each of the electrodes is measured. In other embodiments, instead of, or in addition to, applying sets of voltage patterns, one or more sets of current source patterns are applied to the electrodes and voltages are measured across the electrodes based on injected currents. Application of each signal pattern at a given time, t, to different ones of the electrodes in each helical array differs among the electrodes.

In one implementation multiple sets of electrical signal patterns are applied to the helical arrays $H_j$ with a phase modulation. That is, an increasing phase shift is assigned to each in the sequence of helical arrays $H_j$. For example, for the $k^{th}$ set of patterns, when observing signals applied to the sequence of electrodes in a particular ring, R, a progressively increasing phase shift, Phi, is imparted among the p=12 electrodes. At the $i^{th}$ electrode in the $r^{th}$ ring the phase shift in the applied signal is given by:

$$\Phi = (2\pi k(i-1)/L - 2\pi k(r-1)/R) \text{Mod } 2\pi \quad \quad (4)$$

where Mod is the modulo operator. That is, $\Phi$ is the remainder resulting from division of $(2\pi k(i-1)/L - 2\pi k(r-1)/R)$ by $2\pi$.

With phase modulation, all of the electrodes receive a signal having the same maximum amplitude $A_0$. For example, the amplitude, A, of the $k^{th}$ pattern at the $i^{th}$ electrode on any one of the rings may be given by $$A_{k,i} = A_0 \sin(\omega t + \Phi) \quad (5)$$

or $$A_{k,i} = A_0 \sin(\omega t - \Phi) \quad (6)$$

but in other embodiments electrodes in the helical arrays can be varied with amplitude modulation. For example, the amplitude, A, of the $k^{th}$ pattern at the $i^{th}$ electrode on the $r^{th}$ ring may be given by $$A = A_0 \cos(2\pi k(i-1)/L - 2k(r-1)/R) \quad (7)$$

where, again, $A_0$ is the maximum amplitude. Similar sets of L signals can be generated by replacing the cosine function in Equations (5), (6) or (7) with the sine function.

While embodiments may differ based on whether the signals applied to different ones of the helical arrays $H_j$ are based on phase, amplitude or frequency modulation, a general feature of the disclosed embodiments is that when each set of electrical signals is applied to the electrodes $44_i$ the time varying electric field produced within the volume enclosed by the surface 45 resembles the turning of a helical screw.

Figure 5:
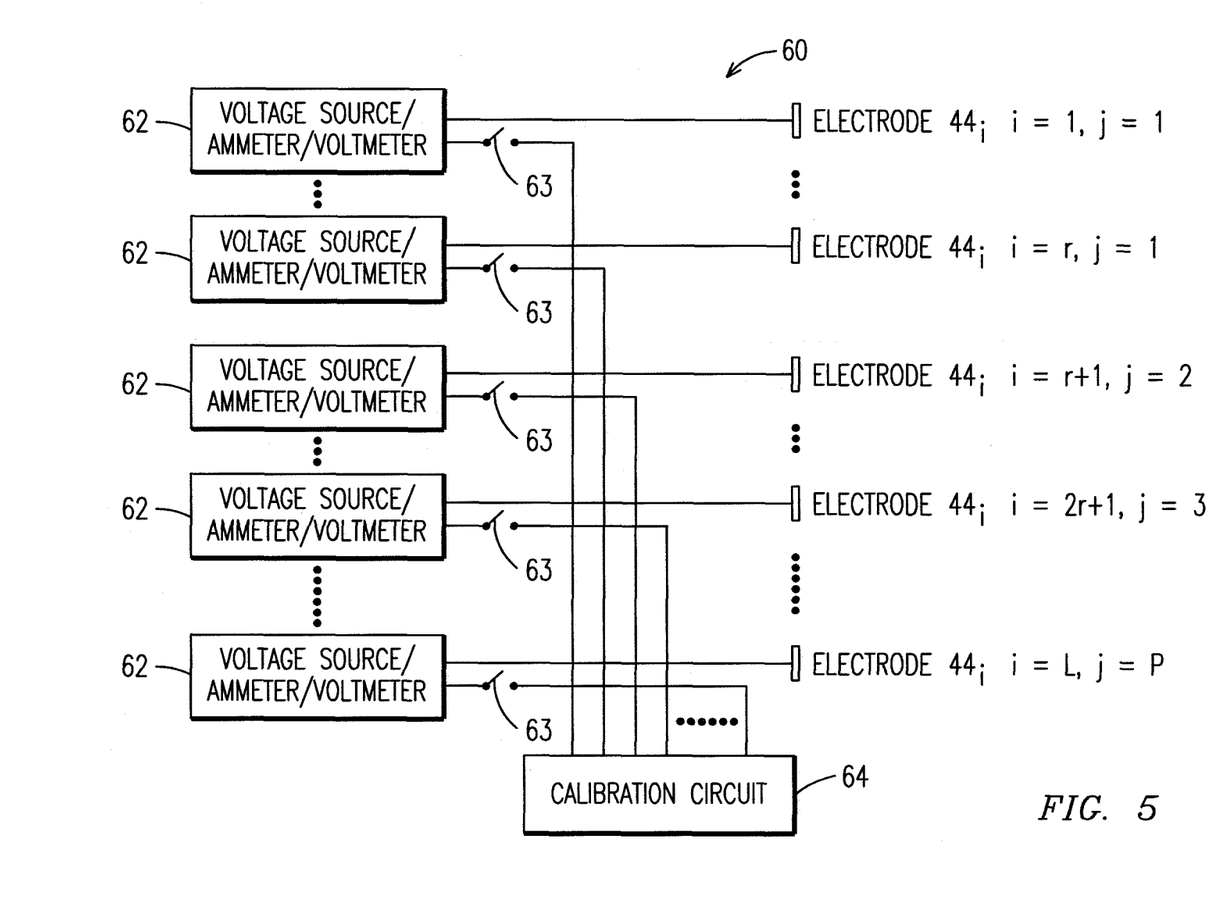
FIG. 5 is a schematic illustration of an circuitry which forms part of the system of FIG. 2.

FIG. 5 is a simplified schematic diagram of an applied-voltage EIT system 60 which forms part of the system 40 of FIG. 2. The system 60 drives p=12 helical arrays $H_j$ each comprising r=12 electrodes $44_i$. The total number of electrodes L=rp=144. In this example, the r electrodes in each array are each connected to a different voltage source circuit $62_i$ to receive a phase, amplitude or frequency modulated voltage signal for generating the field within the volume enclosed by the surface 45. The circuits $62_i$ may include an ammeter to measure current signals generated in response to the applied voltages, and a voltmeter to directly measure the applied voltage. A switching network 63 enables a single calibration circuit 64 to be connected to any of the voltage source/ammeter/voltmeter circuits to allow the whole system to be calibrated to a single reference source. A digital controller (not shown) interfaces with aforementioned components to operate switching functions including calibration, signal generation and acquisition of measurement data. Measurement data is processed according to the invention by the computer 50 to determine the electrical conductivity distribution in the plane P along which the electrodes are positioned.

The electrical conductivity and permittivity distribution is further processed to determine material characteristics of the multi-phase flow, including distribution of different phases or distribution of different materials in the liquid phase, e.g., oil and water. Analysis of the electrical conductivity distribution may determine flow regimes, phase fractions and velocity of individual components of the multi-material system. The flow regimes may, for example, include bubbly flow, churn flow, slug flow, or annular flow.

In voltage source embodiments, current flow between electrodes is a function of relative voltages applied across all electrodes, the conductivity and permittivity distribution along the plane P about which the electrodes are configured. For example, the material may be only oil or it may be an oil-water liquid mixture as well as a separate gas phase. Depending on the distribution of material constituents, the conductivity and permittivity between electrodes will vary and consequently the level of current between electrodes will also vary. Thus, with application of one or more voltage sets and the corresponding measured current data, a matrix of conductivity values corresponding to the varied conductivity along the plane P can be calculated. Because these conductivity values correspond to the conductivities and permittivities of the materials passing through the plane P, by analyzing the conductivities the material composition or phase flow distribution can be determined.

Each set of voltage patterns is a time varying function which contributes to production of a time varying electric field inside the conduit 44, i.e., an electric field which resembles a helix which turns about the axis 47 at an angular velocity which is a function of the applied signal frequency, ω, or integer multiples thereof. For a constant frequency ω, the angular velocity with which the field rotates will be constant. Per the system 60 of FIG. 5, the circuits 62 dedicated to each electrode, all operating under a common clock signal, each generate a waveform having a distinct phase relative to the phase of the waveform generated for the adjacent electrode in the same helical array $H_j$. Thus multiple phase-shifted waveforms are simultaneously applied to different ones of the equally spaced-apart electrodes in each helical array $H_j$ and the electrodes in different ones of the arrays are phase shifted with respect to one another. That is, for p=12 helical arrays $H_j$, which are spaced thirty degrees apart about the axis 47, the signals applied to the sequence of electrodes in the same ring, R, which are members of different helical arrays, each phase have a maximum amplitude $A_0$ which is phase shifted with respect to the signal applied to the next or previous electrode along the ring. Collectively, the time varying input signals generate a twisting electric field pattern which rotates about the axis 47.

In one embodiment, when only the conductivity distribution is to be determined, the total number of sets of voltage patterns applied to the electrodes to acquire complete information about the phase distribution may be as small as k=L/2. The L/2 patterns may be either forward patterns, which produce an electric field which twists in a clockwise direction about the axis 47, or reverse patterns, which produce an electric field which twists in a counter clockwise direction about the axis 47.

A data acquisition process according to an embodiment of the invention sequentially applies k sets of voltage patterns to the electrodes $44_i$. In other embodiments, the sets of applied electrical signals may comprise one or more sets of current values and one or more sets of voltage values. For the purpose of better understanding the first electrical signal set is assumed to be a set of voltage values.

For each set of applied voltage patterns a set of electrical signal patterns is measured, e.g., in accord with the system 60 of FIG. 6. An exemplary number of acquired data elements for each set of applied voltage patterns is the product of the number of electrodes and the number of measurements taken per cycle of applied signal. With the circuitry 48 of the system 40 including A/D converters, for each voltage excitation pattern a time series of current data is recorded for each of the L electrodes. This time series data is processed to extract amplitudes and phases of currents at all L electrodes. Time series data at each electrode provides one amplitude and one phase value for current at that electrode. Hence for L electrodes there are L measurements. The process in repeated for all k sets of voltage patterns to provide kL elements of measured time series data.

Based on the full applied electrical signal set (L, L), the resulting full set of measured electrical signals (L, L), and an inverse of the full applied electrical signal set, an impedance matrix or an admittance matrix representing material distribution in the conduit is determined. In one embodiment, a pseudo inverse may be utilized to determine the inverse of the applied signal set. The calculated matrix is representative of the material distribution in the conduit and is of size (L×L). It is a symmetric matrix with complex entries which is equal to its own transpose—that is, the element in the ith row and jth column of a matrix a is equal to the element in the jth row and ith column of the matrix a, for all indices i and j:

$$a_{i,j} = a_{j,i} \quad (8)$$

Based on kL elements of measured time series data, a conductivity matrix is determined which is representative of the distribution of material in the conduit 46. Image reconstruction is performed based on the conductivity and or admittivity matrix. For further discussion on exemplary determinations of matrix values indicative of material distribution see U.S. application Ser. No. 12/652,116 hereby incorporated by reference.

The applied signal set may be represented by a matrix P and the measured signal set may be represented by a matrix Q. The impedance network is then represented by a matrix Z, where $$Z = P * Q^{-1}. \quad (8)$$

However, the matrix Q is a measured signal set and is an ill posed matrix. Hence it is difficult to find the inverse of this matrix. Thus, calculating admittance matrix is easier in this case since admittance matrix can be calculated as given below:

$$Y = Q * P^{-1}. \quad (9)$$

The applied signal set, e.g., a voltage set, in this case has better fidelity than the measured signal set e.g., a current set. Further, since the applied signal set is known well before hand it can be stored in the computer and its inverse is also stored in the computer. Thus, for determining the admittance matrix the measured signal set is directly multiplied with the available inverse of the applied voltage signal. In one embodiment, the material distribution may also be represented and calculated by an impedance matrix Z, if the applied signal set is a current set M and the measured signal set is a voltage set S. The impedance matrix Z in this case is given by $$Z = S * M^{-1}. \quad (10)$$

In both equations (9) and (10), in one embodiment, a pseudo inverse is utilized to calculate inverses of matrices P and M. The pseudo inverse techniques may include, for example, one-sided inverse, Drazin inverse, Group inverse, Bott-Duffin inverse, or Moore-Penrose pseudo inverse. The inverse calculation technique is thus used to obtain a direct calculation of an impedance matrix or an admittance matrix instead of using a numerical method or an iterative method. The admittance matrix Y and impedance matrix Z of equations (9) and (10) may then be calculated as:

$$Y = Q * ((P^H P)^{-1} * P^T) \quad (11)$$

$$Z = S * ((M^H M)^{-1} * M^T) \quad (12)$$

where, $P^H$ and $M^H$ are conjugate transposes of matrices P and M.

In some process systems, admittance or impedance values of the components of the multi-material system may vary with time. However, since the applied signal set is constant and the measured signal set is measured in real time, a time varying admittance matrix or impedance matrix may also be calculated. In one embodiment, various pre-computed tables or matrices of random flow regime models are stored in the computer and when the system determines the electrical network representation, it is simply compared with stored matrices and thus the flow regime is identified. In another embodiment, the admittance or impedance matrix is analyzed by a heuristic algorithm to determine the phase flow or material distribution. The heuristic algorithm may include a fuzzy logic algorithm or genetic algorithm or neural network algorithm for example. The fuzzy logic algorithm provides a simple way to arrive at a definite conclusion based upon vague, ambiguous, imprecise, noisy, or missing input information. The results of fuzzy logic algorithm are approximate rather than precise. Further, a neural network may be trained to identify flow regimes and compute the likeliest conductivity distribution based on the history of the flow and pre-computed matrices to determine the characteristics of the multi-material system.

A method has been described for displaying an image of an interior of a structure which may be an image of a multi-phase medium, or a medical image of organs or other portions of a human body but, more generally, an image of features within a volume characterized by different electrical properties. In the disclosed embodiments an image is generated to characterize multi-phase fluids (e.g., oil, water and hydrocarbon gas) flowing through a conduit, or a volume containing multiple regions having different conductivities which influence transmission of electrical signals through the volume. The determined image information may be used to estimate relative proportions of liquid and gaseous material flowing through the conduit.

A feature of embodiments of the invention is provision of a series of electrodes positioned in a helical array and provision of multiple such helical arrays of electrodes about a three dimensional surface. Electrical signal sets may be applied to the electrodes with a variety of phase shifts, amplitude or frequency modulations to generate a field useful for characterizing the interior of the structure. With the structure including two or more regions having different conductivities the invention determines an image representative of the interior of the structure in a manner with a more computationally efficient approach to image generation with electrical impedance tomography.

In disclosed embodiments the invention the series of applied electrical signal sets each comprise voltage input patterns and the measured electrical signal sets each comprise measured current levels. In other embodiments the series of applied electrical signal sets each comprise current input patterns and the measured electrical signal sets each comprise measured voltage levels. In still other embodiments some in the series of applied electrical signal sets comprise voltage input patterns while others in the series of applied electrical signal sets comprise current input patterns, and some of the measured electrical signal sets comprise measured current levels while others of the measured electrical signal sets comprise measured voltage levels.

While only certain features of the invention have been illustrated and described herein, many modifications and changes will occur to those skilled in the art. It is, therefore, to be understood that the appended claims are intended to cover all such modifications and changes as fall within the true spirit of the invention.

The claimed invention is:

1. A method for generating data for reconstructing the distribution of electrical properties within a multi-material object comprising:
configuring a plurality of electrodes along a three-dimensional helical path to provide a three dimensional array of electrodes about the multi-material object;
applying a set of signal patterns for input to the electrodes and obtaining, in response to application of the set of signal patterns, a measured set of electrical signals from the electrodes;
calculating, with the measured set of electrical signals, a three-dimensional conductivity or admittivity distribution representative of an interior of the object in a region of the object about which the electrodes are positioned; and determining three-dimensional image data representative of the multi-material region in the object including two or more regions having different conductivities or admittivities.

2. The method of claim 1, wherein multiple sets of signal patterns are sequentially applied to the electrodes and the series of applied electrical signal sets each comprise voltage input patterns and a measured electrical signal set of current levels is obtained for each applied signal set.

3. The method of claim 1 wherein the object is a conduit through which materials having different conductivities flow.

4. The method of claim 3 wherein the materials include oil and a hydrocarbon gas.

5. The method of claim 1 wherein the object is a conduit through which materials having different phases flow.

6. The method of claim 5 wherein image information is used to determine relative proportions of liquid and gaseous material flowing through the conduit.

7. The method of claim 1 further including providing the image data to a display for viewing of an image representative of the interior of the object.

8. A method for generating data for reconstructing the distribution of electrical properties within a multi-material object comprising:

configuring a plurality of electrodes along a three-dimensional helical path to provide a three dimensional array of electrodes about the multi-material object;

applying a set of signal patterns for input to the electrodes and obtaining, in response to application of the set of signal patterns, a measured set of electrical signals from the electrodes wherein the step of configuring the plurality of electrodes includes positioning the electrodes along a series of three-dimensional helical paths to provide p helical arrays each comprising a sequence of r electrodes; and the step of applying the set of signal patterns for input to the electrodes includes, when applying the set of signal patterns to the electrodes at a given time, applying a different signal pattern to different ones of the electrodes.

9. The method of claim 8 wherein each helical array comprises $r_i$ electrodes arranged as an ordered sequence wherein, for a given value of i, the electrodes $r_i$, each associated with a different helix, are positioned along a common plane $P_i$ in a ring-like pattern.

10. The method of claim 8 wherein multiple sets of signal patterns are sequentially applied to the electrodes and the series of applied electrical signal sets each comprise voltage input patterns and a measured electrical signal set of current levels is obtained for each applied signal set.

11. The method of claim 8 wherein the object is a conduit through which materials having different conductivities flow.

12. The method of claim 11 wherein the materials include oil and a hydrocarbon gas.

13. The method of claim 8 wherein the object is a conduit through which materials having different phases flow.

14. The method of claim 13 wherein the image data is used to determine relative proportions of liquid and gaseous material flowing through the conduit.

15. A method for generating data for reconstructing the distribution of electrical properties within a multi-material object comprising:

configuring a plurality of electrodes along a three-dimensional helical path to provide a three dimensional array of electrodes about the multi-material object;

applying a set of signal patterns for input to the electrodes and obtaining, in response to application of the set of signal patterns, a measured set of electrical signals from the electrodes; and calculating, with the measured set of electrical signals, a three-dimensional conductivity or admittivity distribution representative of an interior of the object in a region of the object about which the electrodes are positioned.

16. The method of claim 15 wherein multiple sets of signal patterns are sequentially applied to the electrodes and the series of applied electrical signal sets each comprise voltage input patterns and a measured electrical signal set of current levels is obtained for each applied signal set.

17. The method of claim 15 wherein the object is a conduit through which materials having different conductivities flow.

18. The method of claim 17 wherein the materials include oil and a hydrocarbon gas.

19. The method of claim 15 wherein the object is a conduit through which materials having different phases flow.

20. The method of claim 19 wherein image information is used to determine relative proportions of liquid and gaseous material flowing through the conduit.

* * * * *

UNITED STATES PATENT AND TRADEMARK OFFICE
CERTIFICATE OF CORRECTION

PATENT NO. : 8,508,238 B2
APPLICATION NO. : 12/855018
DATED : August 13, 2013
INVENTOR(S) : Sakethraman Mahalingam et al.

It is certified that error appears in the above-identified patent and that said Letters Patent is hereby corrected as shown below:

In the Specification

In Column 7, Line 63, delete "wiring 45" and insert -- wiring 42 --, therefor.

In Column 8, Line 13, delete "wiring 45" and insert -- wiring 42 --, therefor.

In Column 9, Line 11, in Equation (7), delete " $A = A_0 \cos(2\pi k(i-1)/L - 2k(r-1)/R)$ " and insert -- $A = A_0 \cos(2\pi k(i-1)/L - 2\pi k(r-1)/R)$ --, therefor.

In Column 10, Line 5, delete "conduit 44," and insert -- conduit 46, --, therefor.

In the Claims

In Column 13, Line 34, in Claim 8, delete "electrodes" and insert -- electrodes, --, therefor.

Signed and Sealed this
Twenty-seventh Day of May, 2014

Michelle K. Lee
*Deputy Director of the United States Patent and Trademark Office*